(12) United States Patent
Watanabe et al.

(10) Patent No.: US 10,803,672 B2
(45) Date of Patent: Oct. 13, 2020

(54) DESIGNATION DEVICE, COMPUTER-READABLE RECORDING MEDIUM, AND DESIGNATION DEVICE CONTROL METHOD

(71) Applicants: FUJITSU LIMITED, Kawasaki-shi, Kanagawa (JP); The University of Tokyo, Bunkyo-ku, Tokyo (JP)

(72) Inventors: Masahiro Watanabe, Kawasaki (JP); Machiko Nakagawa, Kawasaki (JP); Toshiaki Hisada, Kashiwa (JP); Seiryo Sugiura, Bunkyo (JP); Takumi Washio, Bunkyo (JP); Jun-ichi Okada, Bunkyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 80 days.

(21) Appl. No.: 16/042,249

(22) Filed: Jul. 23, 2018

(65) Prior Publication Data

US 2019/0035161 A1    Jan. 31, 2019

(30) Foreign Application Priority Data

Jul. 26, 2017    (JP) .................................. 2017-144915

(51) Int. Cl.
*G06T 19/20*    (2011.01)
*A61B 34/10*    (2016.01)
(Continued)

(52) U.S. Cl.
CPC .............. *G06T 19/20* (2013.01); *A61B 34/10* (2016.02); *G06T 7/0014* (2013.01); *G06T 15/08* (2013.01);
(Continued)

(58) Field of Classification Search
None
See application file for complete search history.

(56) References Cited

U.S. PATENT DOCUMENTS 5,687,737 A * 11/1997 Branham ............. A61B 5/0422
                                                              600/523
6,230,048 B1 * 5/2001 Selvester ............... A61B 5/044
                                                              600/523
(Continued)

FOREIGN PATENT DOCUMENTS

JP    2015-223429    12/2015
WO    WO 2010/021309 A1    2/2010

OTHER PUBLICATIONS

Schroeder, W., et al. "The Visualization Toolkit", 2$^{nd}$ Edition, pp. 360-362, 1997.

*Primary Examiner* — Nancy Bitar
(74) *Attorney, Agent, or Firm* — Xsensus LLP

(57) ABSTRACT

A designation device includes a storage that stores therein a three-dimensional model of an organ, and a processor coupled to the storage. The processor executes a process including: first acquiring designations of a plurality of planes of the three-dimensional model of the organ; second acquiring designations of a specific number of pieces of point information indicating an infarct site of the organ for any one or all of the planes; determining the infarct site of the organ that is interposed between the planes on the basis of the pieces of point information; and outputting an image reproducing determination result of the infarct site of the organ at the determining using the three-dimensional model.

11 Claims, 16 Drawing Sheets

(51) Int. Cl.
    *G06T 15/08*    (2011.01)
    *G06T 7/00*     (2017.01)
    *G06T 19/00*    (2011.01)
    *G16H 50/50*    (2018.01)
    *G16H 50/20*    (2018.01)

(52) U.S. Cl.
    CPC ............ *G06T 19/00* (2013.01); *G16H 50/20* (2018.01); *G16H 50/50* (2018.01); *A61B 2034/105* (2016.02); *G06T 2207/30048* (2013.01); *G06T 2219/004* (2013.01); *G06T 2219/2021* (2013.01)

(56) References Cited

U.S. PATENT DOCUMENTS

| | | | | |
|---|---|---|---|---|
| 9,415,135 | B2* | 8/2016 | Healy | A61L 27/16 |
| 9,458,192 | B1* | 10/2016 | Cameron | C07K 5/06026 |
| 9,644,238 | B2* | 5/2017 | Anversa | A61K 35/34 |
| 2003/0023130 | A1* | 1/2003 | Ciaccio | A61B 5/04011 |
| | | | | 600/12 |
| 2009/0099563 | A1* | 4/2009 | Ciaccio | G06T 7/0012 |
| | | | | 606/41 |
| 2011/0123500 | A1* | 5/2011 | Anversa | A61P 9/00 |
| | | | | 424/93.7 |
| 2013/0006131 | A1* | 1/2013 | Narayan | A61B 5/4839 |
| | | | | 600/508 |
| 2015/0348310 | A1 | 12/2015 | Watanabe et al. | |
| 2019/0290717 | A1* | 9/2019 | Lang | C12Y 301/03048 |

\* cited by examiner

FIG.5

NODAL POINT INFORMATION TABLE 121a

| NODAL POINT NUMBER | COORDINATES |
|---|---|
| 1 | 0.00  0.00  0.00 |
| 2 | 0.00  0.00  0.00 |
| ⋮ | ⋮ |
| $N_{nodes}$ | 1.00  2.00  3.00 |

ELEMENT INFORMATION TABLE 121b

| ELEMENT NUMBER | NODAL POINT NUMBER |
|---|---|
| 1 | 1, 2, 3, 4 |
| 2 | 2, 3, 4, 5 |
| ⋮ | ⋮ |
| $N_{mesh}$ | Ni, Nj, Nk, Nl |

FIG.6

INFARCT SITE ELEMENT LIST

| ELEMENT NUMBER | ENTIRE/ PARTIAL | COORDINATES OF PLANE INTERSECTION |
|---|---|---|
| 100 | ENTIRE | |
| 101 | PARTIAL | c, d, e |
| ⋮ | ⋮ | ⋮ |
| $M_{mesh}$ | ENTIRE | |

FIG.11
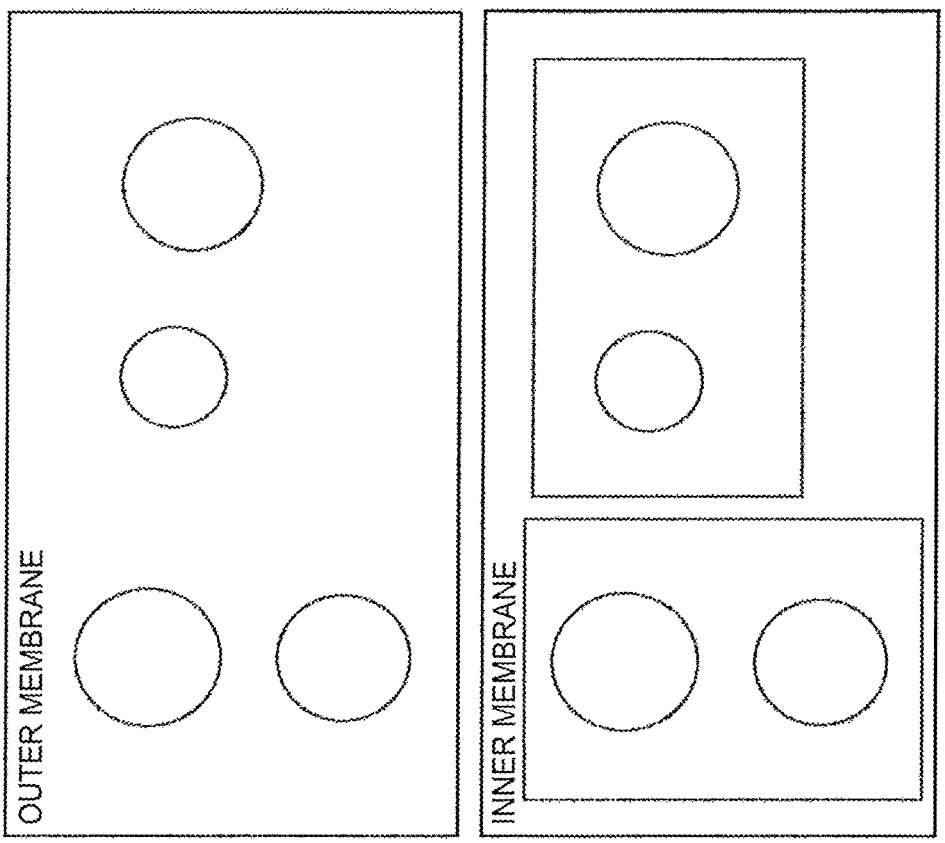
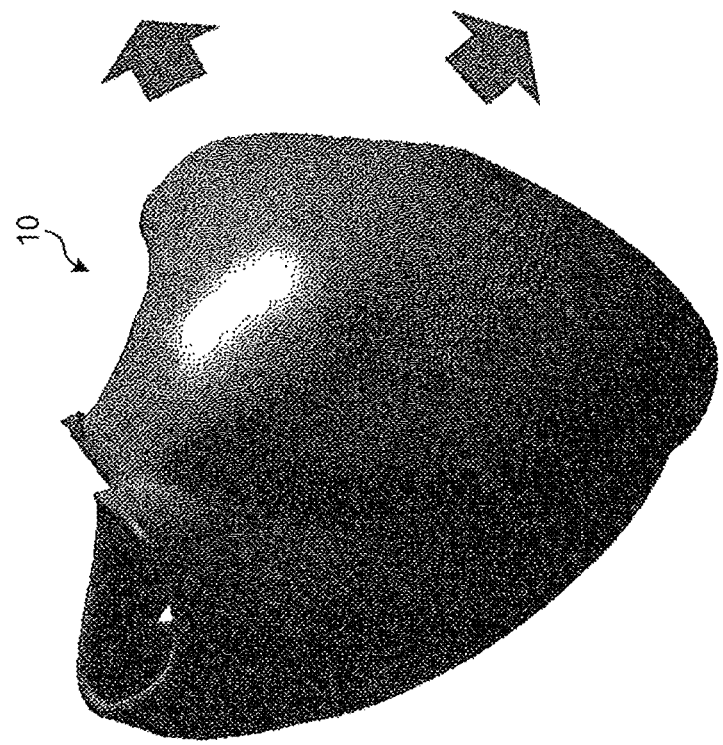

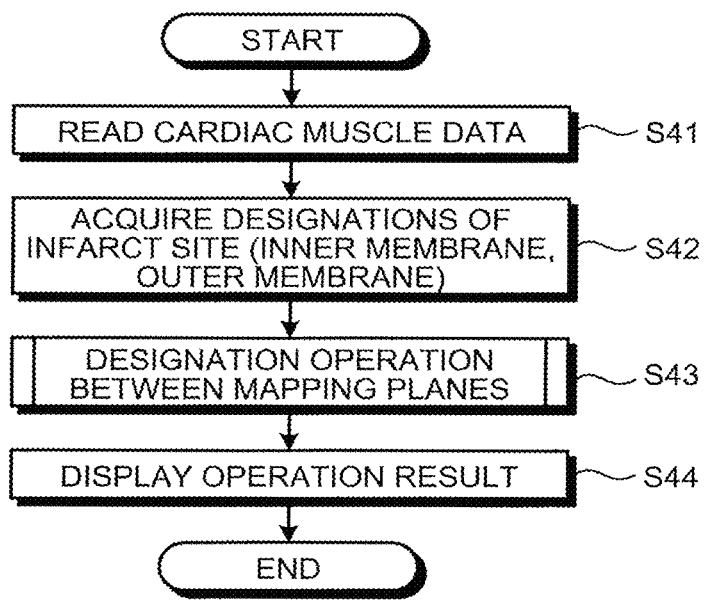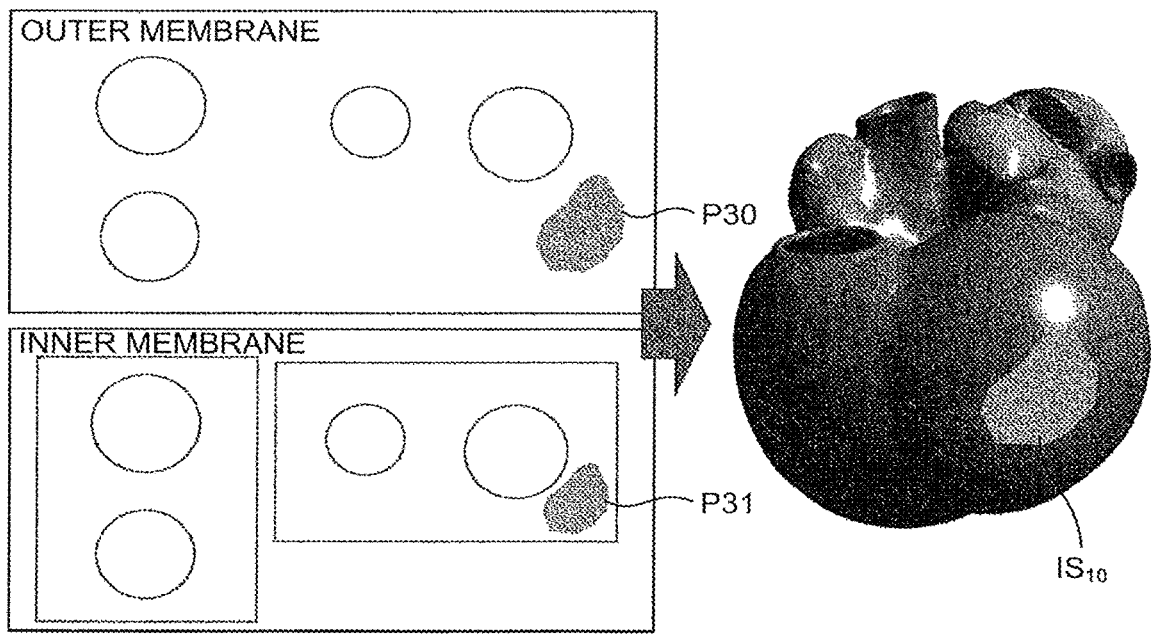

DESIGNATION DEVICE, COMPUTER-READABLE RECORDING MEDIUM, AND DESIGNATION DEVICE CONTROL METHOD

CROSS-REFERENCE TO RELATED APPLICATION

This application is based upon and claims the benefit of priority of the prior Japanese Patent Application No. 2017-144915, filed on Jul. 26, 2017, the entire contents of which are incorporated herein by reference.

FIELD

The embodiments discussed herein are related to a designation device, a computer-readable recording medium, and a designation device control method.

BACKGROUND

Excitation propagation simulation in the heart is one of numerical analyses reproducing functions of the heart. In the excitation propagation simulation, a computer reproduces change in an electrical phenomenon (excitation propagation) on cardiac muscle over time. The excitation propagation simulation reproduces cardiac muscle behavior and an ischemia state of a patient.

In order to reproduce the excitation propagation of the heart, a physician needs to designate an infarct site of the cardiac muscle. The physician designates the infarct site of the cardiac muscle using, for example, a drawing tool. Examples of the drawing tool include Adobe Photoshop (registered trademark). Japanese Laid-open Patent Publication No. 2015-223429 and International Publication Pamphlet No. WO2010/021309 are examples of the conventional technique.

There is however the problem that the conventional technique of designating the infarct site of the cardiac muscle disables the physician to efficiently designate the infarct site of the cardiac muscle. That is to say, when the physician designates the infarct site of the cardiac muscle using the drawing tool, he(she) draws it using a pointing device such as a mouse and therefore has difficulty in efficiently designating the infarct site of the cardiac muscle.

SUMMARY

According to an aspect of an embodiment, a designation device includes a storage that stores therein a three-dimensional model of an organ, and a processor coupled to the storage. The processor executes a process including: first acquiring designations of a plurality of planes of the three-dimensional model of the organ; second acquiring designations of a specific number of pieces of point information indicating an infarct site of the organ for any one or all of the planes; determining the infarct site of the organ that is interposed between the planes on the basis of the pieces of point information; and outputting an image reproducing determination result of the infarct site of the organ at the determining using the three-dimensional model.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 5 is a view illustrating an example of a data structure of a nonstructural lattice data storage unit;

FIG. 6 is a view illustrating an example of a data structure of an infarct site element list;

FIG. 11 is a view for explaining mapping development;

FIG. 13 is a view illustrating a flowchart of processing of the designation device in the second embodiment;

FIG. 14 is a view illustrating a display example of an infarct site of the heart in the second embodiment;

DESCRIPTION OF EMBODIMENTS

Preferred embodiments of the present invention will be explained with reference to accompanying drawings. It is to be noted that the embodiments do not limit the present invention.

[a] First Embodiment

Figure 1:
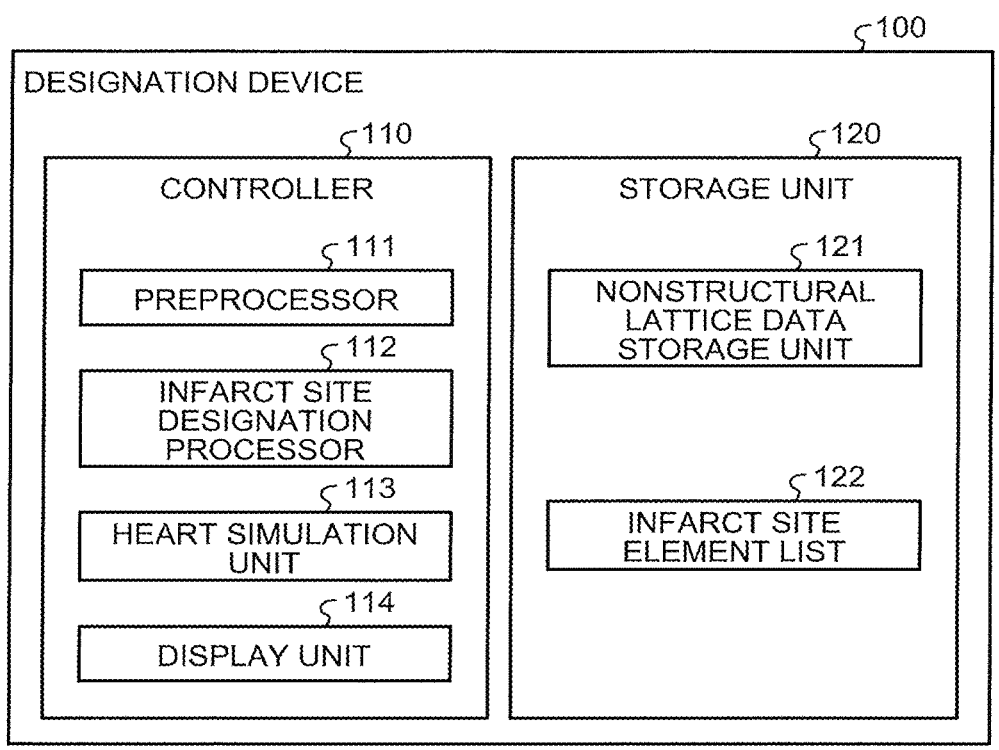
FIG. 1 is a block diagram illustrating the functional configuration of a designation device according to a first embodiment.

FIG. 1 is a functional block diagram illustrating the configuration of a designation device according to a first embodiment. A designation device 100 illustrated in FIG. 1 efficiently acquires designation of an infarct site of cardiac muscle when simulation of the heart as one type of organs is supposed to be performed.

The designation device 100 includes a controller 110 and a storage unit 120.

The storage unit 120 is, for example, a semiconductor memory element such as a random access memory (RAM) and a flash memory or a storage device such as a hard disk and an optical disc. The storage unit 120 includes a nonstructural lattice data storage unit 121 and an infarct site element list 122.

The nonstructural lattice data storage unit 121 stores therein nonstructural lattice data indicating a shape of the heart three-dimensionally as a three-dimensional model of the heart. The nonstructural lattice data represents the shape of the heart with a plurality of tetrahedral elements, for example. In this case, a large number of nodal points are provided in a space in which the heart is present. A large number of tetrahedrons with four nodal points as vertices are defined. One tetrahedron is an element representing, for example, a myocardial cell of the heart. Hereinafter, one tetrahedron is referred to as an element in some cases. An example of the data structure of the nonstructural lattice data storage unit 121 will be described later.

The infarct site element list 122 is information indicating elements that are determined as the infarct site in a list form. An infarct site designation processor 112, which will be described later, is used to designate the infarct site. The infarct site element list 122 is a set of collected elements that a heart simulation unit 113 determines as the infarct site. An example of the data structure of the infarct site element list 122 will be described later.

The controller 110 corresponds to an operation processing device such as a central processing unit (CPU). The controller 110 has an internal memory for storing therein programs defining various processing procedures and pieces of control data, and executes various pieces of processing by them. The controller 110 includes a preprocessor 111, the infarct site designation processor 112, the heart simulation unit 113, and a display unit 114.

The preprocessor 111 performs preprocessing of infarct site designation on the basis of the three-dimensional model of the heart.

The preprocessor 111, for example, acquires designations of cross-sectional positions of the heart using the three-dimensional model of the heart. The preprocessor 111 acquires designations of at least two cross-sectional positions. The designation of the cross-sectional position is, for example, information defining a plane encompassing a cross section. For example, a user executing the heart simulation performs the designation.

The preprocessor 111 acquires designations of segments indicating boundaries between an atrium and ventricular myocardium using the three-dimensional model of the heart. That is to say, the preprocessor 111 acquires designations of four points (measurement points) indicating two boundaries between the atrium and the ventricular myocardium in order to exclude the right atrium side. The preprocessor 111 acquires designations of a cardiac axis position and a segment indicating radius information about the cardiac axis position using the three-dimensional model of the heart. That is to say, the preprocessor 111 acquires designations of two points (measurement points) indicating the cardiac axis position and the radius information about the cardiac axis position. For example, the user executing the heart simulation performs the designation.

The infarct site designation processor 112 performs infarct site designation processing on the basis of the three-dimensional model of the heart. For example, the infarct site designation processor 112 acquires, for each of the cross sections designated by the preprocessor 111, designations of a specific number of pieces of point information among pieces of point information defined on the cross section previously or by designation using the three-dimensional model of the heart. A closed region formed by the pieces of point information designated for each of the cross sections is a region of the infarct site of the heart on each cross section. The specific number of pieces of point information is, for example, four. For example, the user executing the heart simulation performs the designation. Although the specific number of pieces of point information is four in the above description, it is sufficient that it is equal to or more than three.

Figure 2:
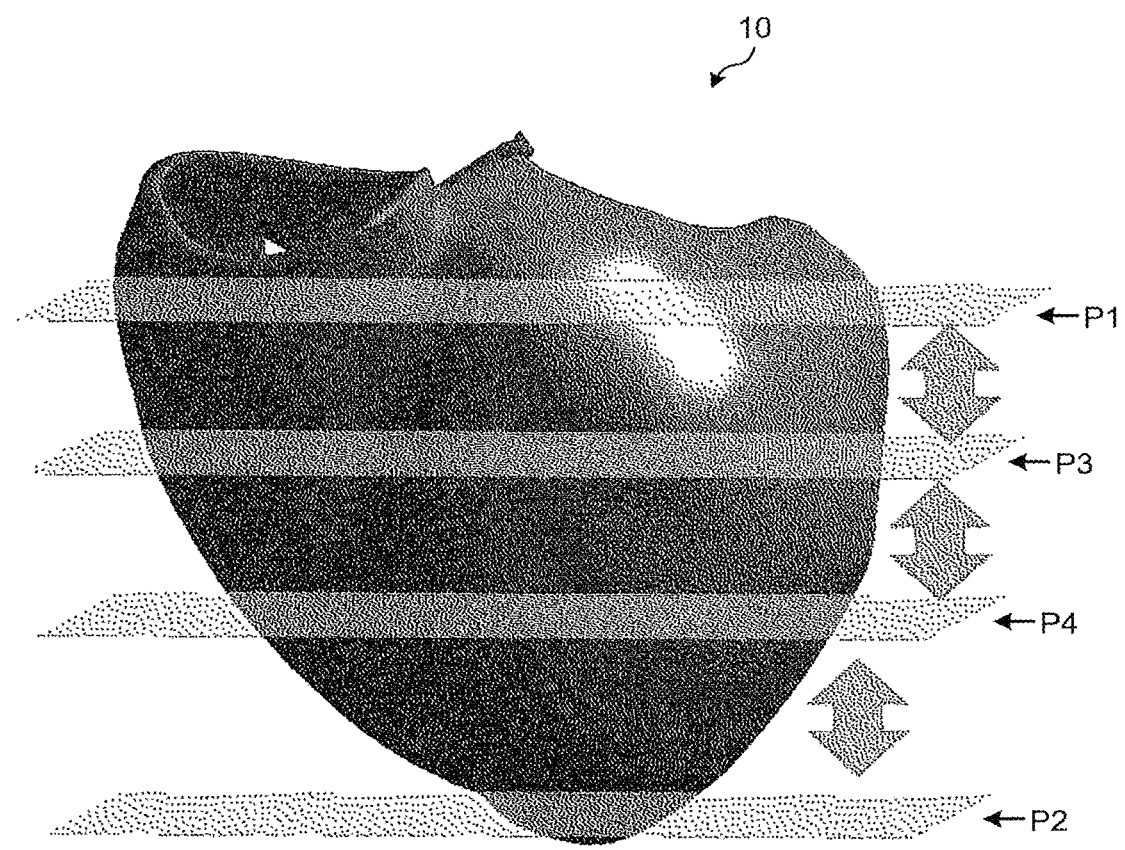
FIG. 2 is a view for explaining designation of cross-sectional positions.

Designation of the cross-sectional positions and designation of the infarct site will be described with reference to FIG. 2 and FIG. 3. FIG. 2 is a view for explaining the designation of the cross-sectional positions. In an example of FIG. 2, a three-dimensional model 10 of the heart is illustrated. The three-dimensional model 10 is a set of the tetrahedral elements.

As illustrated in FIG. 2, the preprocessor 111 acquires the designations of the cross-sectional positions of the ventricle of the heart. In this example, designation of a cross-sectional position at a position close to an annulus, which is indicated by reference numeral P1, is acquired. Designation of a cross-sectional position at a position close to a cardiac apex, which is indicated by reference numeral P2, is acquired. Designations of cross-sectional positions at positions of cross sections between the cross section indicated by the reference numeral P1 and the cross section indicated by the reference numeral P2, which are indicated by reference numeral P3 and reference numeral P4, may be further acquired.

Figure 3:
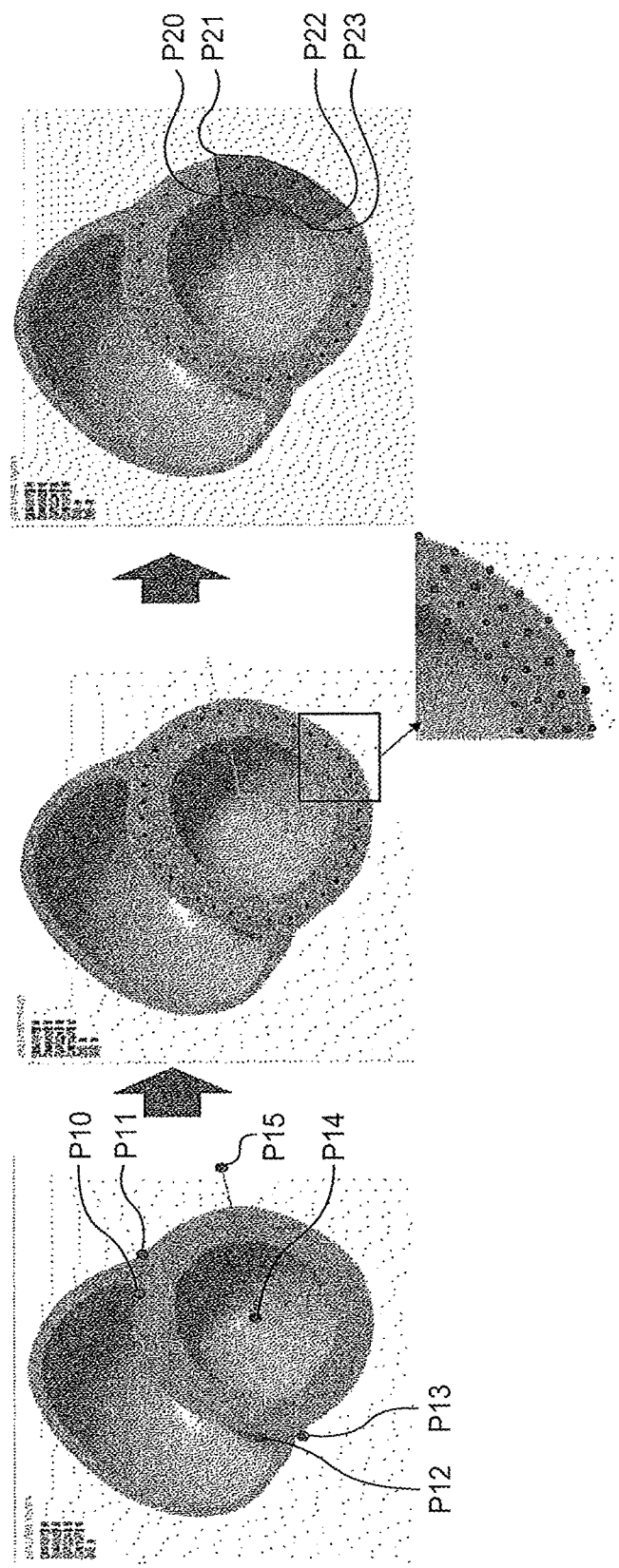
FIG. 3 is a view for explaining infarct site designation processing.

FIG. 3 is a view for explaining the infarct site designation processing. In an example of FIG. 3, a three-dimensional model of one cross section of the heart is illustrated. The three-dimensional model is a set of the tetrahedral elements.

As illustrated in a left view in FIG. 3, the preprocessor 111 acquires the designations of the segments indicating the boundaries between the atrium and the ventricular myocardium. In this example, designations P10 and P11 at two points indicating one boundary between the atrium and the ventricular myocardium are acquired. Designations P12 and P13 at two points indicating another boundary between the atrium and the ventricular myocardium are acquired. The preprocessor 111 can thereby exclude the right atrium side when designating the infarct site at the left atrium side, for example.

The preprocessor 111 acquires the designations of the cardiac axis position and the segment indicating the radius information about the cardiac axis position. In this example, the preprocessor 111 acquires designations P14 and P15 at two points indicating the cardiac axis position and the radius information about the cardiac axis position. The preprocessor 111 can thereby acquire positions as points of origin to be used for arrangement (definition) of internally dividing points on the cross section.

As illustrated in a middle view in FIG. 3, the preprocessor 111 arranges the internally dividing points for division into n in the 360-degree circumferential direction of the cardiac muscle and division into m in the thickness direction of the cardiac muscle. The internally dividing points may be previously defined. The preprocessor 111 may arrange the internally dividing points for division into n in the 360-degree circumferential direction and division into m in the thickness direction after acquiring designations of values of n and m. In this example, it is assumed that n is 36 and m is 4.

As illustrated in a right view in FIG. 3, the infarct site designation processor 112 acquires designations of the specific number of pieces of point information indicating the infarct site of the heart. When the specific number thereof is assumed to be four, designations P20, P21, P23, and P24 at four points are acquired. A closed region formed by the designated four points is the infarct site of the heart on the cross section.

In FIG. 3, when the user executing the heart simulation designates the infarct site of the heart, he(she) can efficiently designate the infarct site of the heart by designating 10 points for each cross section.

With reference to FIG. 1 again, the heart simulation unit 113 simulates determination of the region of the infarct site between the cross sections on the basis of the three-dimensional model of the heart. That is to say, the heart simulation unit 113 determines the region of the infarct site of the heart that is interposed between the cross sections on the basis of the specific numbers of pieces of point information indicating the infarct site, the pieces of point information having been acquired for each of the cross sections by the infarct site designation processor 112. The heart simulation unit 113 stores a simulation result in the infarct site element list 122. The determination of the region of the infarct site is performed by designation operation between the cross sections.

Figure 4:
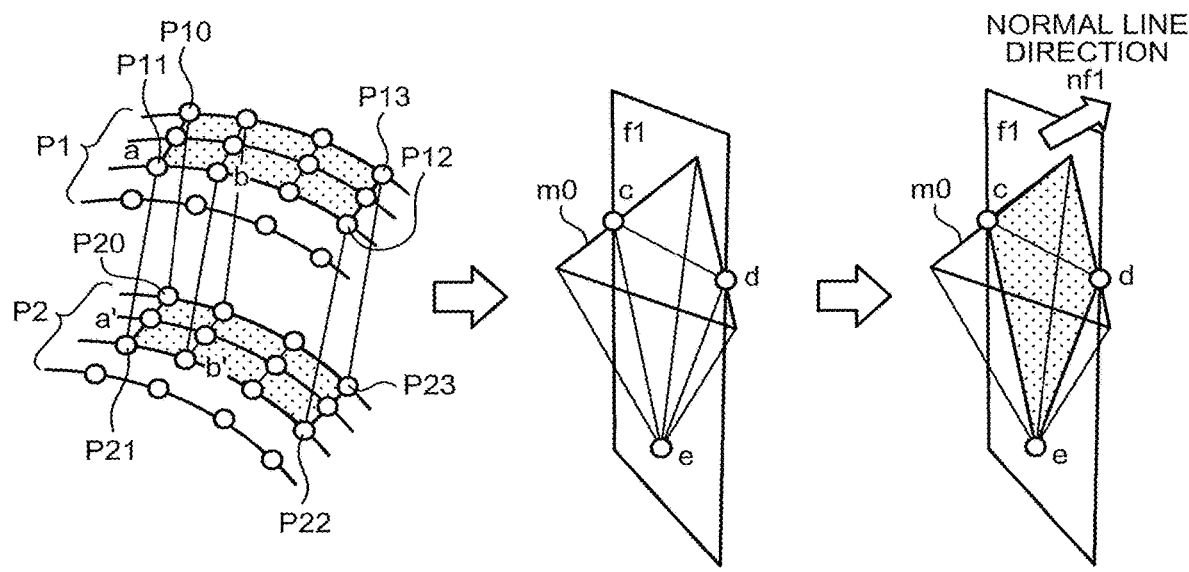
FIG. 4 is a view for explaining an example of designation operation between cross sections.

The designation operation between the cross sections will be described with reference to FIG. 4. FIG. 4 is a view for explaining the designation operation between the cross sections. It is assumed that the preprocessor 111 has acquired the designations of the two cross-sectional positions indicated by the reference numeral P1 and the reference numeral P2. It is assumed that the infarct site designation processor 112 has acquired the four designations P10, P11, P12, and P13 indicating the infarct site of the heart on the cross section P1. It is assumed that the infarct site designation processor 112 has acquired the four designations P20, P21, P22, and P23 indicating the infarct site of the heart on the cross section P2. That is to say, the infarct site designation processor 112 regards a three-dimensional closed region formed by the points designated by the user as the region of the infarct site of the heart.

Under this condition, the heart simulation unit 113 selects the element from the three-dimensional model as the set of the tetrahedral elements one by one and performs determination of the infarct site on the selected element. For example, when a selected element m0 is fully contained in the closed region, the heart simulation unit 113 stores, in the infarct site element list 122, information indicating that the selected element m0 is entirely the infarct site.

On the other hand, when the selected element m0 is not fully contained in the closed region, the heart simulation unit 113 determines whether the selected element m0 intersects with any of a plurality of cross-sectional functions indicating cross sections of respective faces (cross sections) of the closed region designated by the user using the cross-sectional functions. In a left view in FIG. 4, the heart simulation unit 113 specifies, as abb'a', a cross-sectional function f1 indicating the cross section of each face (cross section) of the closed region designated by the user. In a middle view in FIG. 4, when the selected element m0 intersects with the specified cross-sectional function f1, the heart simulation unit 113 extracts an intersection plane. In this example, an intersection plane cde is extracted.

In a right view in FIG. 4, the heart simulation unit 113 determines the infarct site by determining whether all of the normal line directions of the cross-sectional function f1 direct to the inner side of the closed region with respect to the extracted intersection plane cde. That is to say, when all of the normal line directions of the cross-sectional function f1 direct to the inner side of the closed region, the heart simulation unit 113 determines that a portion of the element m0 on the normal line direction side relative to the intersection plane is the infarct site. In this example, when all of normal line directions nf1 of the cross-sectional function f1 direct to the inner side of the closed region with respect to the extracted intersection plane cde, the heart simulation unit 113 determines that a portion of the element m0 on the normal line direction nf1 side relative to the intersection plane cde is the infarct site. When the heart simulation unit 113 determines that the portion of the element m0 is the infarct site, it stores, in the infarct site element list 122, information on the element m0 that is partially contained in the closed region. As an example, the information on the element m0 includes coordinates of intersections of the intersection plane.

When any of the normal line directions of the cross-sectional function does not direct to the inner side of the closed region with respect to the intersection plane, the heart simulation unit 113 determines that the element m0 is not the infarct site.

The display unit 114 displays, on a monitor, an image reproducing a state of determination of the infarct site of the heart with the three-dimensional model.

Example of Data Structure of Nonstructural Lattice Data Storage Unit

An example of the data structure of the nonstructural lattice data storage unit 121 will be described with reference to FIG. 5. FIG. 5 is a diagram illustrating an example of the data structure of the nonstructural lattice data storage unit. As illustrated in FIG. 5, the nonstructural lattice data storage unit 121 includes, for example, a nodal point information table 121a and an element information table 121b. In the nodal point information table 121a, a nodal point number and coordinates indicating the position of a nodal point are set for each nodal point. In the element information table 121b, an element number and the nodal point numbers of nodal points corresponding to apexes of a tetrahedral element are set for each element. The three-dimensional model of the heart is generated on the basis of the pieces of data stored in the nonstructural lattice data storage unit 121 illustrated in FIG. 5.

Example of Data Structure of Infarct Site Element List

An example of the data structure of the infarct site element list 122 will be described with reference to FIG. 6. FIG. 6 is a view illustrating an example of the data structure of the infarct site element list. As illustrated in FIG. 6, in the infarct site element list 122, the element number, entire/partial, and coordinates of plane intersections are set for each element. The entire/partial indicates whether the entire element is the infarct site or a part of the element is the infarct site. When the entire element is the infarct site, "entire" is set, whereas when a part of the element is the infarct site, "partial" is set. The coordinates of the plane intersections indicate the coordinates of the intersections of the intersection plane between the cross-sectional function and the element when a part of the element is the infarct site.

Flowchart of Processing of Designation Device

Figure 7:
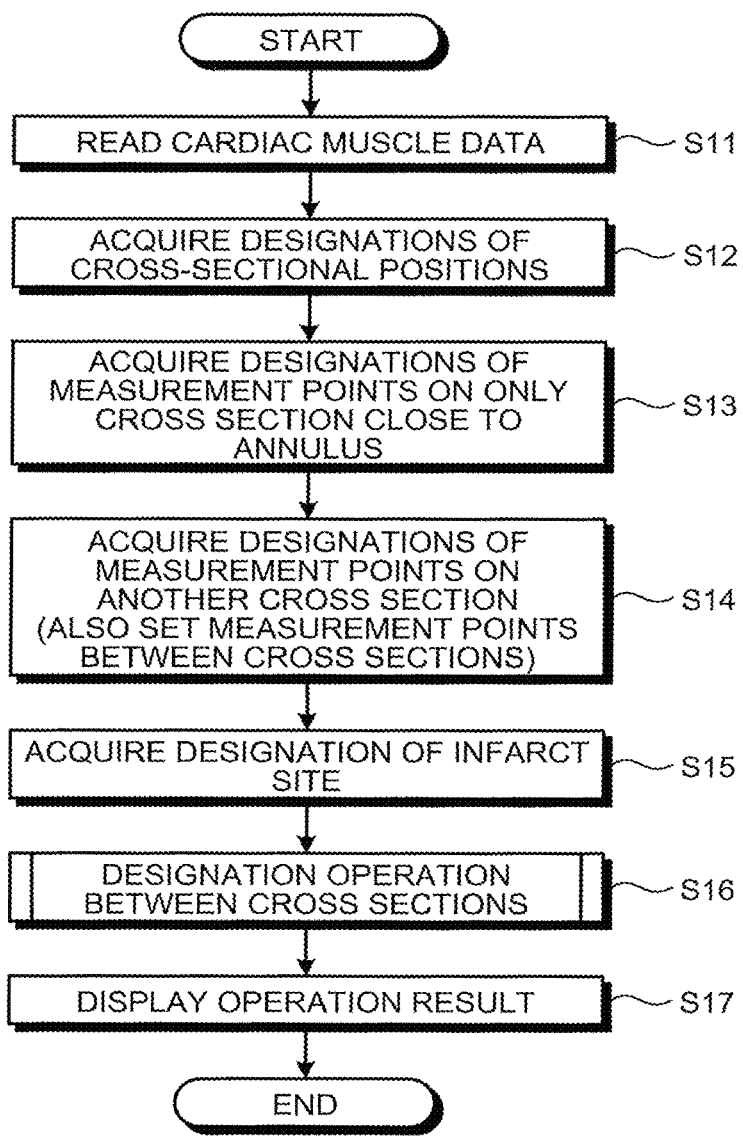
FIG. 7 is a view illustrating a flowchart of the designation device in the first embodiment.

FIG. 7 is a view illustrating a flowchart of the designation device in the first embodiment.

As illustrated in FIG. 7, the preprocessor 111 reads cardiac muscle data from a three-dimensional model of the heart (step S11). The preprocessor 111 acquires designations of cross-sectional positions using the cardiac muscle data (step S12). The preprocessor 111, for example, grasps the three-dimensional model of the heart on the basis of the nodal points indicated in the nodal point information table 121a and the elements indicated in the element information table 121b with reference to the nonstructural lattice data storage unit 121 to acquire pieces of data indicating the surfaces of the three-dimensional model.

The preprocessor 111 acquires designations of measurement points on only a cross section close to the annulus using the cardiac muscle data (step S13). The preprocessor 111 acquires, for example, designations of four points (measurement points) indicating the two boundaries between the atrium and the ventricular myocardium. The right atrium side is thereby excluded. The preprocessor 111 acquires designations of two points (measurement points) indicating the cardiac axis position and the radius information about the cardiac axis position.

Then, the preprocessor 111 acquires designations of measurement points on another cross section using the cardiac muscle data (step S14). The preprocessor 111 acquires, for example, designations of six measurement points on another cross section differing from the cross section close to the annulus in the same manner. The preprocessor 111 may also acquire designations of six measurement points on a cross section between the cross section close to the annulus and the aforementioned other cross section.

Subsequently, the infarct site designation processor 112 acquires designation of the infarct site using the cardiac muscle data (step S15). The infarct site designation processor 112 acquires, for each of the cross sections acquired by the preprocessor 111, designations of the specific number of pieces of point information among the pieces of point information defined on the cross section, for example. The closed region formed by the pieces of point information designated for each of the cross sections is the region of the infarct site of the heart on the cross section.

Thereafter, the heart simulation unit 113 performs designation operation between the cross sections (step S16). The flowchart of the designation operation processing between the cross sections will be described later.

The display unit 114 displays an operation result (step S17). The display unit 114 displays, for example, on the monitor, an image reproducing a state of determination of the infarct site of the heart with a three-dimensional model.

Flowchart of Designation Operation Processing Between Cross Sections

Figure 8:
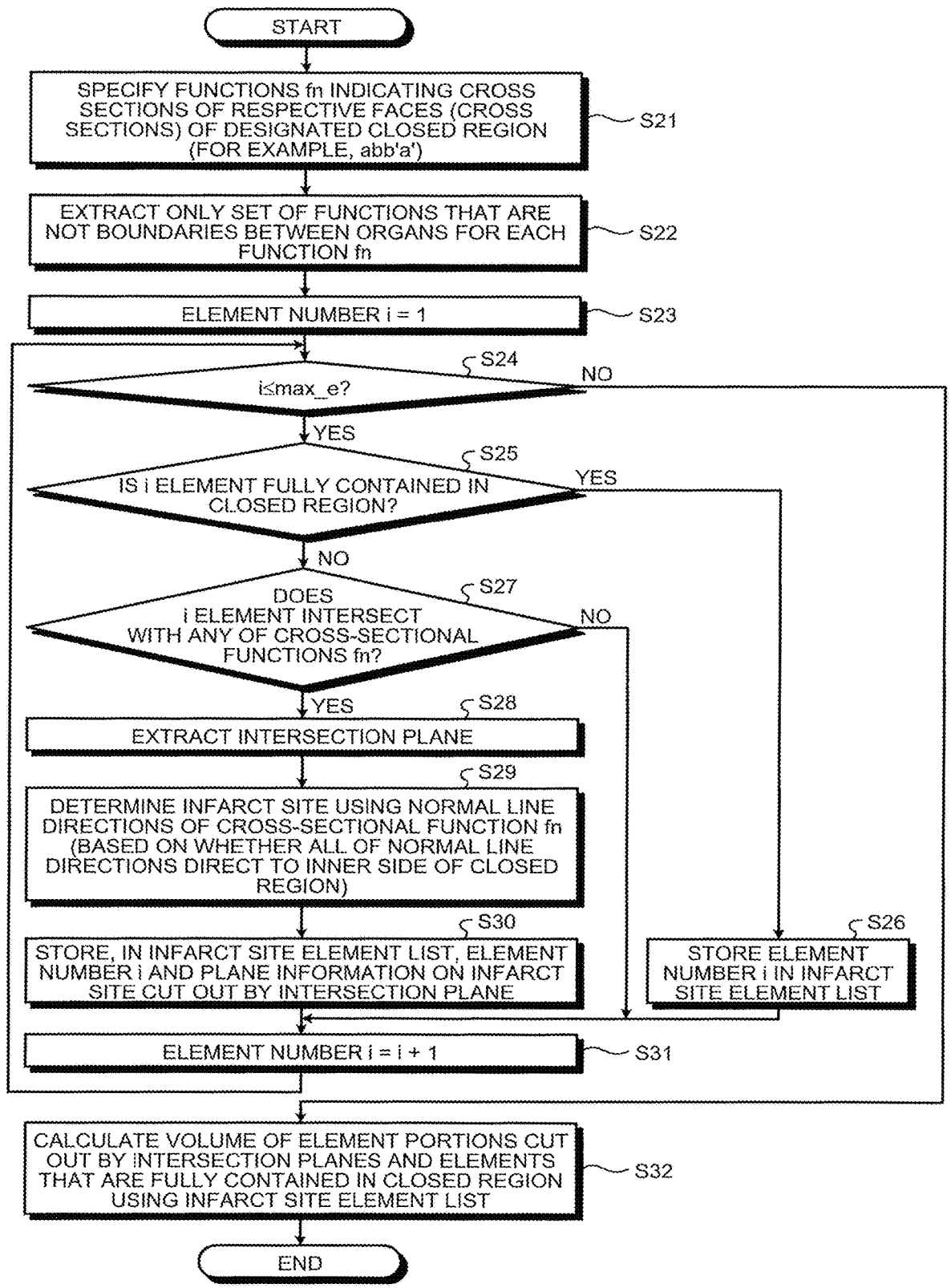
FIG. 8 is a view illustrating a flowchart of designation operation processing between the cross sections.

FIG. 8 is a view illustrating a flowchart of the designation operation processing between the cross sections in the first embodiment.

As illustrated in FIG. 8, the heart simulation unit 113 specifies the functions fn indicating the cross sections of the respective faces (cross sections) of the designated closed region (step S21). The function fn is, for example, a function indicating abb'a' in the left view in FIG. 4.

The heart simulation unit 113 extracts only a set of functions that do not indicate boundaries between organs for each function fn (step S22). Then, the heart simulation unit 113 sets an initial value "1" to a variable i (step S23). A value set to the variable i is the element number.

The heart simulation unit 113 determines whether the variable i is equal to or smaller than max_e indicating a maximum value of the element number (step S24). When the heart simulation unit 113 determines that the variable i is equal to or smaller than max_e (Yes at step S24), the heart simulation unit 113 determines whether the element indicated by the variable i is fully contained in the closed region (step S25). When the heart simulation unit 113 determines that the element indicated by the variable i is fully contained in the closed region (Yes at step S25), the heart simulation unit 113 stores the element number i in the infarct site element list (step S26). Then, the heart simulation unit 113 shifts to step S31 to process the next element.

On the other hand, when the heart simulation unit 113 determines that the element indicated by the variable i is not fully contained in the closed region (No at step S25), the heart simulation unit 113 determines whether the element indicated by the variable i intersects with any of the cross-sectional functions fn (step S27). When the heart simulation unit 113 determines that the element indicated by the variable i intersects with none of the cross-sectional functions fn (No at step S27), the heart simulation unit 113 shifts to step S31 to process the next element.

On the other hand, when the heart simulation unit 113 determines that the element indicated by the variable i intersects with any of the cross-sectional functions fn (Yes at step S27), the heart simulation unit 113 extracts an intersection plane (step S28). The intersection plane indicates, for example, the plane with c, d, and e in the middle view in FIG. 4.

Then, the heart simulation unit 113 determines the infarct site using the normal line directions of the specified function fn (step S29). That is to say, when all of the normal line directions direct to the inner side of the closed region, the heart simulation unit 113 determines that a portion of the element indicated by the variable i on the normal line direction side relative to the intersection plane is the infarct site.

The heart simulation unit 113 stores, in the infarct site element list 122, the element number i and plane information on the infarct site cut out by the intersection plane (step S30). Then, the heart simulation unit 113 shifts to step S31 to process the next element.

At step S31, the heart simulation unit 113 increments a value of the variable i (increases by 1) and shifts the processing to step S24.

When it is determined that the variable i is larger than max_e at step S24 (No at step S24), the heart simulation unit 113 calculates the volume of the element portions cut out by the intersection planes and the elements that are fully contained in the closed region using the infarct site element list 122 (step S32). That is to say, the heart simulation unit 113 calculates the volume of the region of the infarct site. The heart simulation unit 113 then ends the designation operation processing.

Display Example

Figure 9:
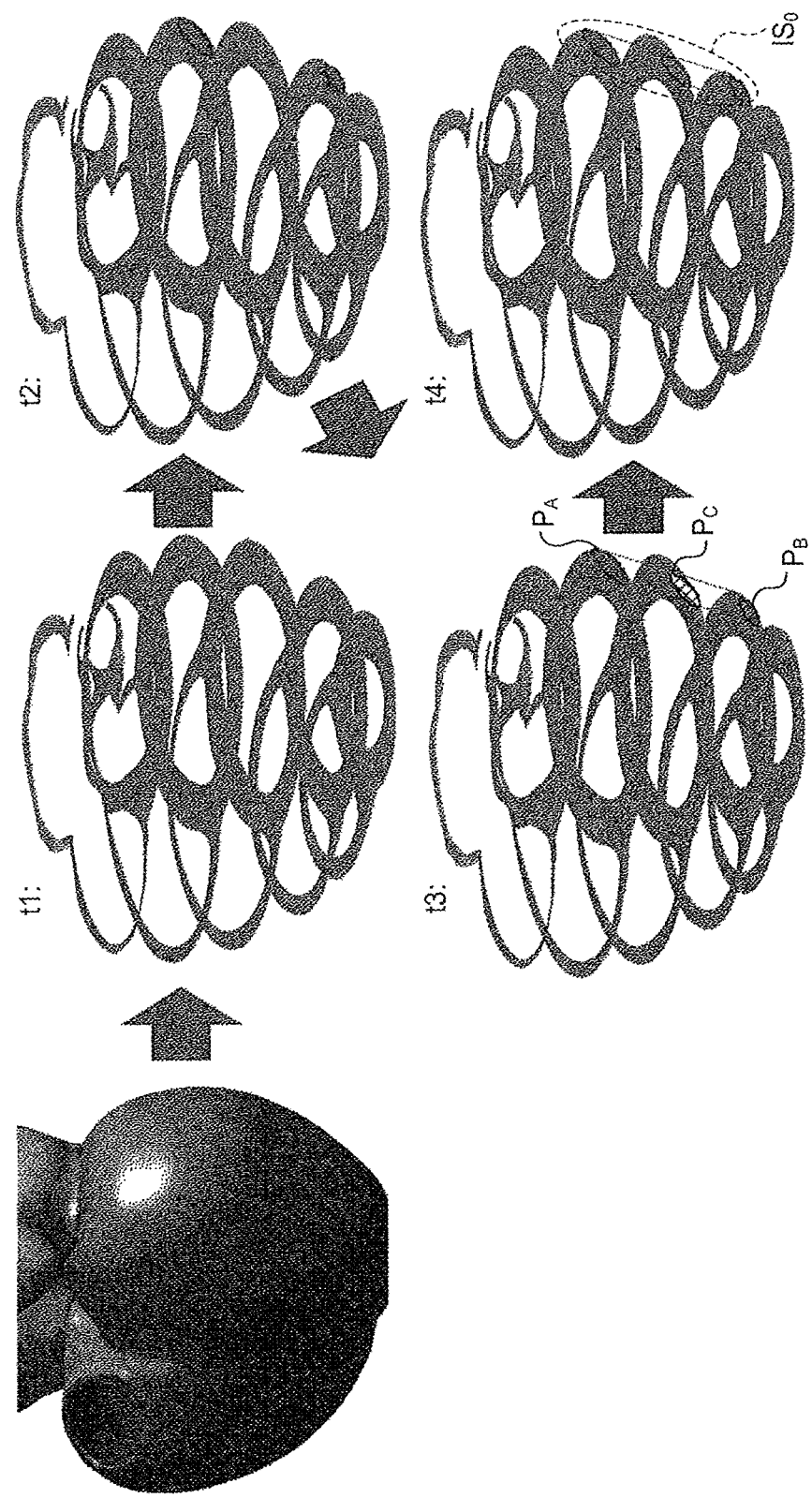
FIG. 9 is a view illustrating a display example of an infarct site of the heart in the first embodiment.

FIG. 9 is a view illustrating a display example of the infarct site of the heart in the first embodiment. In FIG. 9, a state of determination of the infarct site of the heart over time is represented by the three-dimensional model.

As illustrated in FIG. 9, the display unit 114 displays, at a time point of t1, the three-dimensional model of the heart in a form of mesh data using the nonstructural lattice data storage unit 121. The display unit 114 displays, at a time point of t2, positions of the infarct site designated by the infarct site designation processor 112 at the cross-sectional positions of the ventricle of the heart that have been designated by the preprocessor 111 on the mesh data. In this example, $P_A$ and $P_B$ are the positions of the infarct site.

The display unit 114 displays, at a time point of t3, a position of the infarct site designated by the infarct site designation processor 112 at another cross-sectional position of the ventricle of the heart that has been designated by the preprocessor 111 on the mesh data. In this example, $P_C$ is the position of the infarct site.

The display unit 114 displays, at a time point of t4, the infarct site on the mesh data using the infarct site element list 122 provided by the designation operation between the cross sections by the heart simulation unit 113. In this example, $IS_0$ is the infarct site.

Thus, in the above-mentioned first embodiment, the designation device 100 acquires the designations of the planes of the three-dimensional model of the heart. The designation device 100 acquires the designations of the specific number(s) of pieces of point information indicating the infarct site of the heart for any one or all of the planes. The designation device 100 determines the infarct site of the heart that is interposed between the planes on the basis of the specific numbers of pieces of acquired point information. The designation device 100 displays an image reproducing the determination of the infarct site of the heart with the three-dimensional model. This configuration enables the designation device 100 to efficiently designate the infarct site of the cardiac muscle.

The designation device 100 acquires the designations of the cross-sectional positions of the three-dimensional model of the heart. The designation device 100 acquires, for each of the cross sections, the designations of the specific number of pieces of point information among the pieces of point information defined on the cross section previously or by designation. This configuration enables the designation device 100 to designate the cross-sectional positions and designate the specific number of points for each cross section, thereby efficiently designating the infarct site of the cardiac muscle. It is sufficient that the designation device 100 designates six points as the designations of the measurement points and four points as the designations of the infarct site on one cross section, thereby efficiently designating the infarct site of the cardiac muscle.

The designation device 100 determines the infarct site of the heart that is interposed between one cross section and another cross section on the basis of the pieces of point information designated on the one cross section and the pieces of point information on the other cross section that correspond to the pieces of point information on the one cross section. This configuration enables the designation device 100 to visualize the infarct site of the heart accurately.

[b] Second Embodiment

In the first embodiment, the designation device 100 acquires the designations of the specific numbers of pieces of point information indicating the infarct site of the heart for the cross sections and determines the infarct site of the heart that is interposed between the cross sections on the basis of the specific numbers of pieces of acquired point information. The designation device 100 is however not limited to perform the above processing and may acquire designations of the specific numbers of pieces of point information indicating an infarct site of the heart on two mapping planes and determine the infarct site of the heart that is interposed between the two mapping planes on the basis of the specific numbers of pieces of acquired point information. The two mapping planes herein indicate planes (development view) provided by two-dimensional mapping development of an inner membrane and an outer membrane of a three-dimensional ventricle.

In the second embodiment, the designation device 100 acquires the designations of the specific numbers of pieces of point information indicating the infarct site of the heart on the two mapping planes and determines the infarct site of the heart that is interposed between the two mapping planes on the basis of the specific numbers of pieces of acquired point information.

Configuration of Designation Device in Second Embodiment

Figure 10:
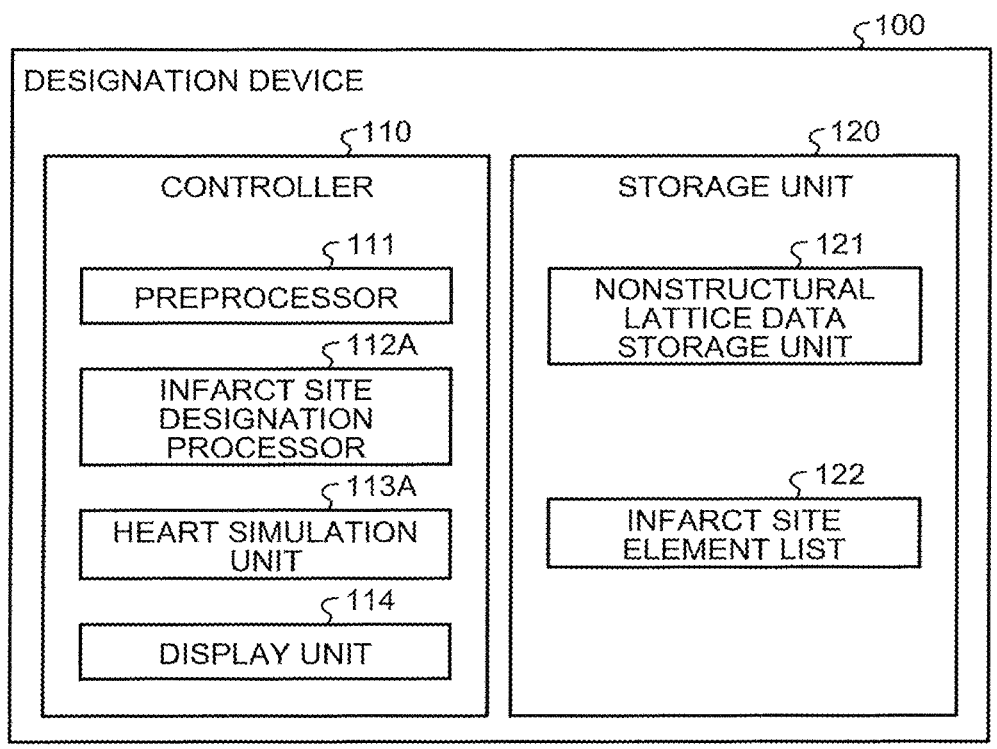
FIG. 10 is a block diagram illustrating the functional configuration of a designation device according to a second embodiment.

FIG. 10 is a functional block diagram illustrating the configuration of a designation device according to a second embodiment. The same reference numerals denote the same configurations as those of the designation device 100 illustrated in FIG. 1 and overlapped description of the configurations and operations thereof is omitted. The first embodiment is different from the second embodiment in that the infarct site designation processor 112 is changed to an infarct site designation processor 112A. The first embodiment is different from the second embodiment in that the heart simulation unit 113 is changed to a heart simulation unit 113A.

The infarct site designation processor 112A acquires designations of mapping planes of an inner membrane and an outer membrane of a ventricle.

The infarct site designation processor 112A designates the infarct site on the basis of the mapping planes of the inner membrane and the outer membrane of the ventricle. The infarct site designation processor 112A acquires, for example, designations of the specific number of pieces of point information using the mapping plane of the inner membrane of the ventricle. The infarct site designation processor 112A acquires designations of the specific number of pieces of point information using the mapping plane of the outer membrane of the ventricle. A closed region formed by the pieces of point information designated for each of the two mapping planes is a region of the infarct site of the heart on each mapping plane. The specific number of pieces of point information is, for example, 10 or 20 but is not limited thereto. For example, a user executing heart simulation performs the designation. The same specific number of points are designated as the points indicating the infarct site of the inner membrane of the ventricle and the points indicating the infarct site of the outer membrane of the ventricle.

The heart simulation unit 113A simulates determination of a region of the infarct site between the mapping planes on the basis of the mapping planes of the inner membrane and the outer membrane of the ventricle. That is to say, the heart simulation unit 113A determines the region of the infarct site of the heart that is interposed between the mapping plane of the inner membrane of the ventricle and the mapping plane of the outer membrane of the ventricle on the basis of the specific numbers of pieces of point information indicating the infarct site, the pieces of point information having been acquired by the infarct site designation processor 112A. The heart simulation unit 113A stores a simulation result in the infarct site element list 122. The determination of the region of the infarct site is performed by designation operation between the mapping planes. The designation operation processing between the mapping planes is similar to the processing described for the heart simulation unit 113 and description of this processing is therefore omitted.

The mapping development of the inner membrane and the outer membrane of the ventricle and the designation of the infarct site will be described with reference to FIG. 11 and FIG. 12. FIG. 11 is a view for explaining the mapping development. In an example of FIG. 11, the three-dimensional model 10 of the heart is illustrated. The three-dimensional model 10 is a set of tetrahedral elements.

An upper right view in FIG. 11 is a view provided by the mapping development of the outer membrane indicating the outer side of the heart. A lower right view in FIG. 11 is a view provided by the mapping development of the inner membrane indicating the inner side of the heart. Respective circles on the planes provided by the mapping development indicate positions of valves of the heart. The planes of the inner membrane and the outer membrane are previously provided by the mapping development from the three-dimensional model of the heart and pieces of information on the planes of the inner membrane and the outer membrane are stored in the storage unit 120. The planes are referred to as "mapping planes".

Figure 12:
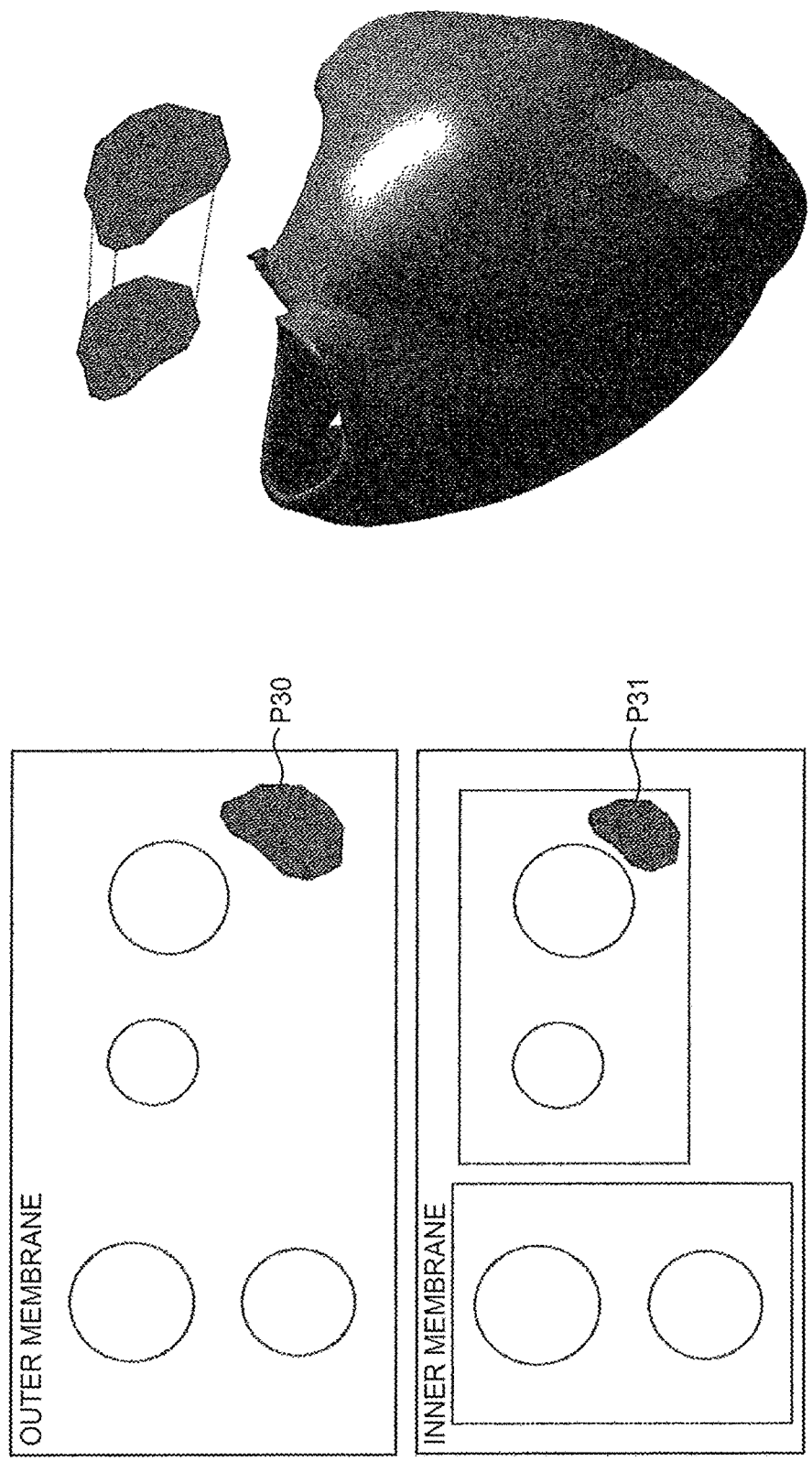
FIG. 12 is a view for explaining infarct site designation processing.

FIG. 12 is a view for explaining infarct site designation processing. In an example of left views in FIG. 12, the mapping plane of the outer membrane of the ventricle and the mapping plane of the inner membrane of the ventricle are illustrated. In an example of a right view in FIG. 12, the three-dimensional model of the heart is illustrated.

As illustrated in an upper left view in FIG. 12, the infarct site designation processor 112A acquires designations of the specific number of pieces of point information using the mapping plane of the outer membrane of the ventricle. A closed region formed by the pieces of point information designated on the mapping plane of the outer membrane of the ventricle is a region of the infarct site of the heart on the mapping plane. In this example, a region P30 is the region of the infarct site of the heart on the mapping plane of the outer membrane of the ventricle. As illustrated in a lower left view in FIG. 12, the infarct site designation processor 112A acquires designations of the same number of pieces of point information as the specific number for designation of the outer membrane using the mapping plane of the inner membrane of the ventricle. In this example, a region P31 is the region of the infarct site of the heart on the mapping plane of the inner membrane of the ventricle.

Thereafter, the heart simulation unit 113A determines a region of the infarct site of the heart that is interposed between the two regions using the region of the infarct site of the outer membrane and the region of the infarct site of the inner membrane, the regions having been acquired by the infarct site designation processor 112A. That is to say, as illustrated in the right view in FIG. 12, the heart simulation unit 113A connects corresponding points of the designated region of the infarct site on the inner membrane of the ventricle and the designated region of the infarct site on the outer membrane of the ventricle to determine the region of the infarct site of the heart that is interposed between the two regions.

With this configuration, when the user executing the heart simulation designates the infarct site of the heart, he(she) can efficiently designate the infarct site of the heart by designating the specific number of points for each of the mapping planes of the outer membrane and the inner membrane of the ventricle.

Flowchart of Processing of Designation Device

FIG. 13 is a view illustrating a flowchart of processing of the designation device in the second embodiment.

As illustrated in FIG. 13, the preprocessor 111 reads cardiac muscle data from a three-dimensional model of the heart (step S41).

The infarct site designation processor 112A acquires designations of an infarct site on an inner membrane and an outer membrane of a ventricle using the cardiac muscle data (step S42). The infarct site designation processor 112A acquires, for example, designations of the specific number of pieces of point information using a mapping plane of the inner membrane of the ventricle. The infarct site designation processor 112A acquires designation of the specific number of pieces of point information using a mapping plane of the outer membrane of the ventricle.

Thereafter, the heart simulation unit 113A performs designation operation between the mapping planes (step S43). The designation operation processing between the mapping planes is similar to the designation operation processing between the cross sections in FIG. 8 and description thereof is therefore omitted.

The display unit 114 displays an operation result (step S44). The display unit 114 displays, for example, on the monitor, an image reproducing a state of determination of the infarct site of the heart with the three-dimensional model.

Display Example

FIG. 14 is a view illustrating a display example of the infarct site of the heart in the second embodiment. An upper left view in FIG. 14 illustrates the mapping plane of the outer membrane on which the region P30 of the infarct site is designated. A lower left view in FIG. 14 illustrates the mapping plane of the inner membrane on which the region P31 of the infarct site is designated.

As illustrated in a right view in FIG. 14, the display unit 114 displays the infarct site on the three-dimensional model using the infarct site element list 122 provided by the designation operation between the mapping planes by the heart simulation unit 113A. In this example, $IS_{10}$ is the infarct site.

Thus, in the above-mentioned second embodiment, the designation device 100 acquires the designations of the mapping plane of the inner membrane and the mapping plane of the outer membrane of the three-dimensional model of the heart. The designation device 100 acquires the designations of the specific number of pieces of point information indicating the infarct site of the heart for each of the two mapping planes. The designation device 100 determines the infarct site of the heart that is interposed between the planes on the basis of the specific numbers of pieces of acquired point information. The designation device 100 outputs an image reproducing the determination of the infarct site of the heart with the three-dimensional model. This configuration enables the designation device 100 to efficiently designate the infarct site of the cardiac muscle.

In the above-mentioned second embodiment, the designation device 100 acquires the designations of the specific number of pieces of point information indicating a range that is estimated to be the infarct site of the heart for each of the mapping planes. This configuration enables the designation device 100 to designate the infarct site more easily than the case of using a drawing tool.

In the above-mentioned second embodiment, the designation device 100 determines the infarct site of the heart that is interposed between the two mapping planes on the basis of the pieces of point information designated for each of the two mapping planes. This configuration enables the designation device 100 to display the infarct site of the heart accurately.

[c] Third Embodiment

In the first embodiment, the designation device 100 acquires the designations of the specific numbers of pieces of point information indicating the infarct site of the heart for the cross sections and determines the infarct site of the heart that is interposed between the cross sections on the basis of the specific numbers of pieces of acquired point information (method A). In the second embodiment, the designation device 100 acquires the designations of the specific numbers of pieces of point information indicating the infarct site of the heart for the two mapping planes of the inner membrane and the outer membrane of the ventricle and determines the infarct site of the heart that is interposed between the two mapping planes on the basis of the specific numbers of pieces of acquired point information (method B). The designation device 100 may however determine the infarct site of the heart using both of the two methods.

In a third embodiment, the designation device 100 determines the infarct site of the heart using both of the two methods of the method A and the method B.

Figure 15:
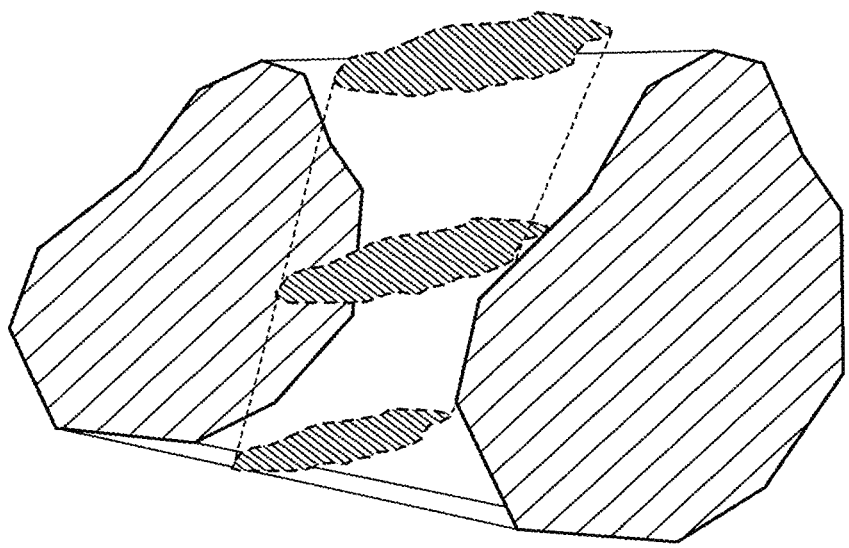
FIG. 15 is a view for explaining heart simulation processing according to a third embodiment.

Heart simulation processing in the third embodiment will be described with reference to FIG. 15. FIG. 15 is a view for explaining the heart simulation processing in the third embodiment.

As illustrated in FIG. 15, first, the heart simulation unit 113A selects any one region of a region indicated by segments with solid lines and a region indicated by segments with dashed lines and determines the infarct site of the heart in the selected region first. Thereafter, the heart simulation unit 113A determines the infarct site of the heart using the other region. When the other region selected later includes a region outside the one region selected first, the heart simulation unit 113A adds the region to the infarct site. That is to say, the heart simulation unit 113A integrates the region of the infarct site with the method A and the region of the infarct site with the method B. Any of the method A and the method B may be performed first.

Flowchart of Processing of Designation Device

Figure 16:
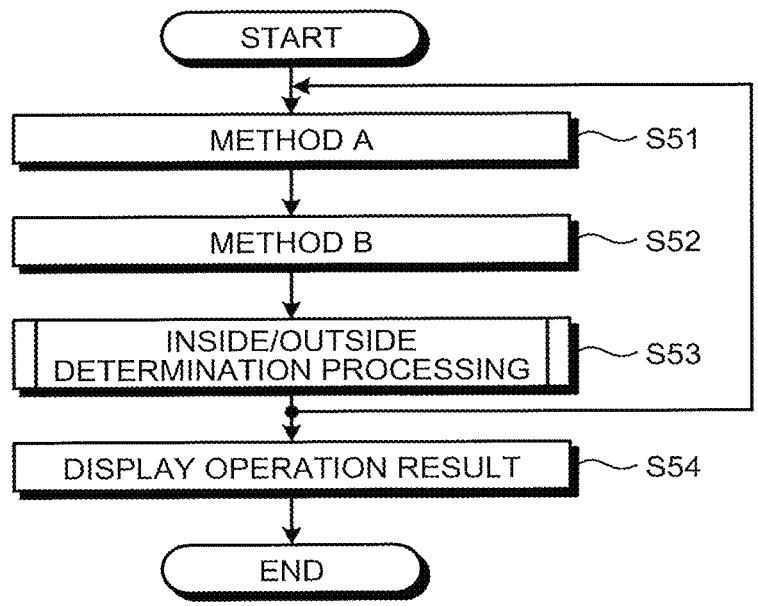
FIG. 16 is a view illustrating a flowchart of processing of a designation device in the third embodiment.

FIG. 16 is a view illustrating a flowchart of processing of the designation device in the third embodiment. Although FIG. 16 illustrates the case in which the method A is performed prior to the method B, the method B may be performed prior to the method A.

As illustrated in FIG. 16, the designation device 100 executes the method A (step S51). That is to say, the designation device 100 acquires the designations of the specific numbers of pieces of point information indicating the infarct site of the heart for the cross sections and determines the infarct site of the heart that is interposed between the cross sections on the basis of the specific numbers of pieces of acquired point information. The designation device 100 stores a determination result in the infarct site element list 122. That is to say, the designation device 100 stores, in the infarct site element list 122, the pieces of information on the respective elements that are entirely or partially contained in the closed region between the designated cross sections.

Then, the designation device 100 executes the method B (step S52). That is to say, the designation device 100 acquires the designations of the specific numbers of pieces of point information indicating the infarct site of the heart for the two mapping planes of the inner membrane and the outer membrane of the ventricle and determines the infarct site of the heart that is interposed between the two mapping planes on the basis of the specific numbers of pieces of acquired point information. The designation device 100 stores a determination result in the infarct site element list 122. That is to say, the designation device 100 stores, in the infarct site element list 122, the pieces of information on the respective elements that are entirely or partially contained in the closed region between the designated mapping planes.

Subsequently, the designation device 100 executes inside/outside determination processing (step S53). A flowchart of the inside/outside determination processing will be described later. The designation device 100 shifts the processing to step S51 and repeatedly performs the processing.

The designation device 100 displays an operation result (step S54). That is to say, the designation device 100 displays, on the monitor, an image reproducing a state of determination of the infarct site of the heart with the three-dimensional model using an integrated result (integrated list) provided by integrating the result of the method A and the result of the method B.

Inner/Outer Determination Processing

Figure 17:
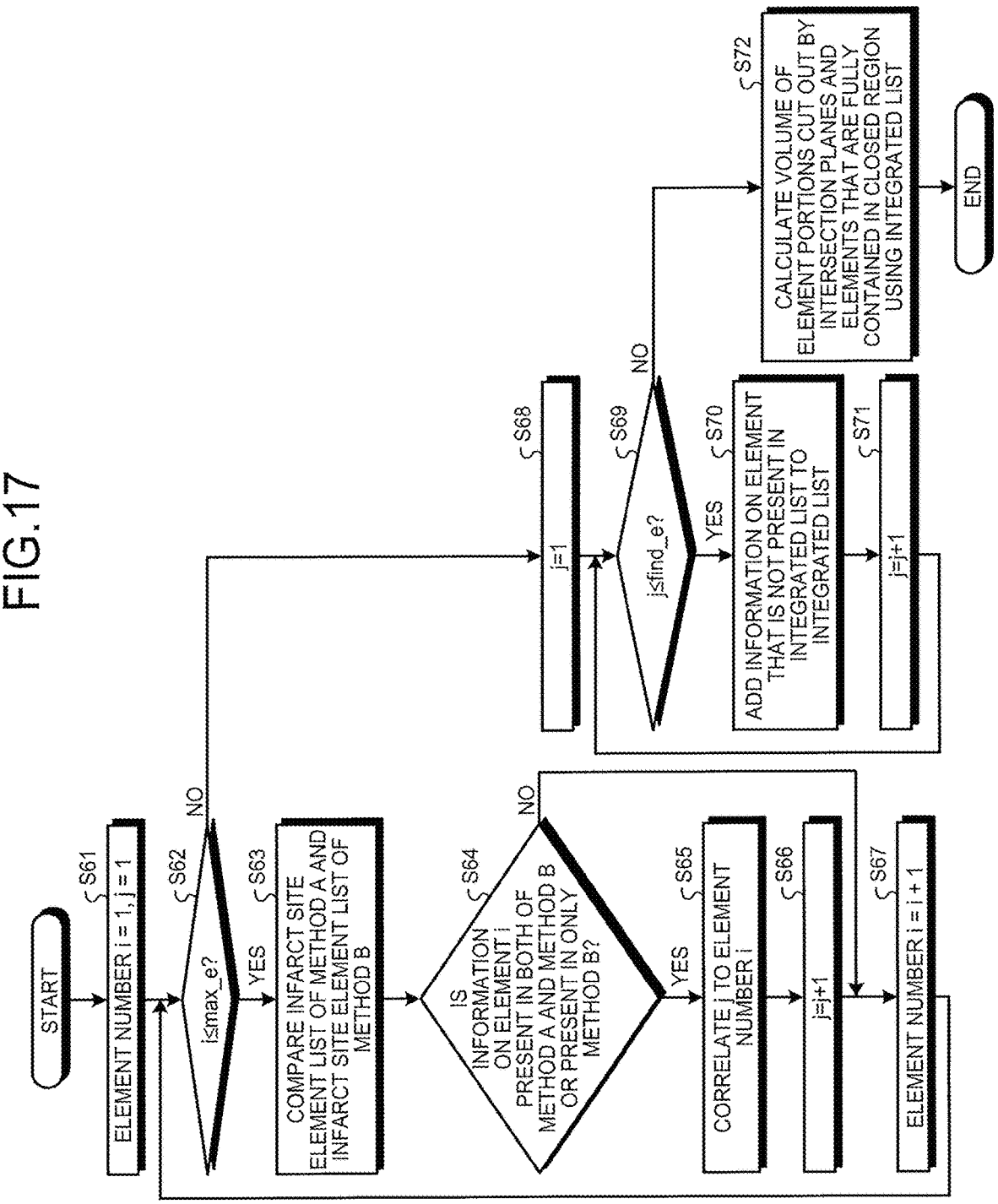
FIG. 17 is a view illustrating a flowchart of inside/outside determination processing.

FIG. 17 is a view illustrating a flowchart of the inside/outside determination processing. In FIG. 17, a list provided by integrating the infarct site element list 122 of the method A and the infarct site element list 122 of the method B is referred to as an "integrated list".

As illustrated in FIG. 17, the designation device 100 sets an initial value "1" to a variable i and sets an initial value "1" to a variable j (step S61). The designation device 100 determines whether the variable i is equal to or smaller than max_e indicating a maximum value of the element number (step S62).

When it is determined that the variable i is equal to or smaller than max_e (Yes at step S62), the designation device 100 compares the infarct site element list 122 of the method A and the infarct site element list 122 of the method B (step S63). The designation device 100 determines whether information on the element i is present in both of the method A and the method B or is present in only the method B processed later (step S64).

When the designation device 100 determines that the information on the element i is present in both of the method A and the method B or is present in only the method B processed later (Yes at step S64), it correlates the variable j to the element number i (step S65). The designation device 100 increments a value of the variable j (increases by 1) (step S66) and shifts the processing to step S67.

When the designation device 100 determines that the information on the element i is present in neither of the method A nor the method B or is present in only the method A processed first (No at step S64), it shifts the processing to step S67.

At step S67, the designation device 100 increments a value of the variable i (increases by 1) (step S67) and shifts the processing to step S62.

At step S62, when it is determined that the variable i is larger than max_e (No at step S62), the designation device 100 sets a value obtained by subtracting 1 from the value of the variable j to find_e and shifts the processing to step S68. It is to be noted that find_e indicates the present number of elements i the pieces of information on which are present in both of them or present in only the method B processed later.

At step S68, the designation device 100 sets the initial value "1" to the variable j (step S68). The designation device 100 determines whether the variable j is equal to or smaller than find_e indicating the present number of elements (step S69). When it is determined that the variable j is equal to or smaller than find_e (Yes at step S69), the designation device 100 adds information on an element that is not present in the integrated list to the integrated list (step S70).

The designation device 100 increments the value of the variable j (increases by 1) (step S71) and shifts the processing to step S69.

When it is determined that the variable j is larger than find_e at step S69 (No at step S69), the designation device 100 calculates the volume of the element portions cut out by the intersection planes and the elements that are fully contained in the closed region using the integrated list (step S72). That is to say, the designation device 100 calculates the volume of the region of the infarct site. The designation device 100 then ends the inside/outside determination processing.

In this manner, the designation device 100 integrates the results provided by execution of different methods of the method A and the method B, thereby visualizing the infarct site of the heart more accurately than the case of using the result executed by one method only.

In the first embodiment and the second embodiment, for example, the designation device 100 performs the infarct site designation processing. The infarct site designation processing is not limited to be performed in this manner and may be performed at a calculation service base of a cloud, for example.

Example of Application of Infarct Site Designation Processing

Figure 18:
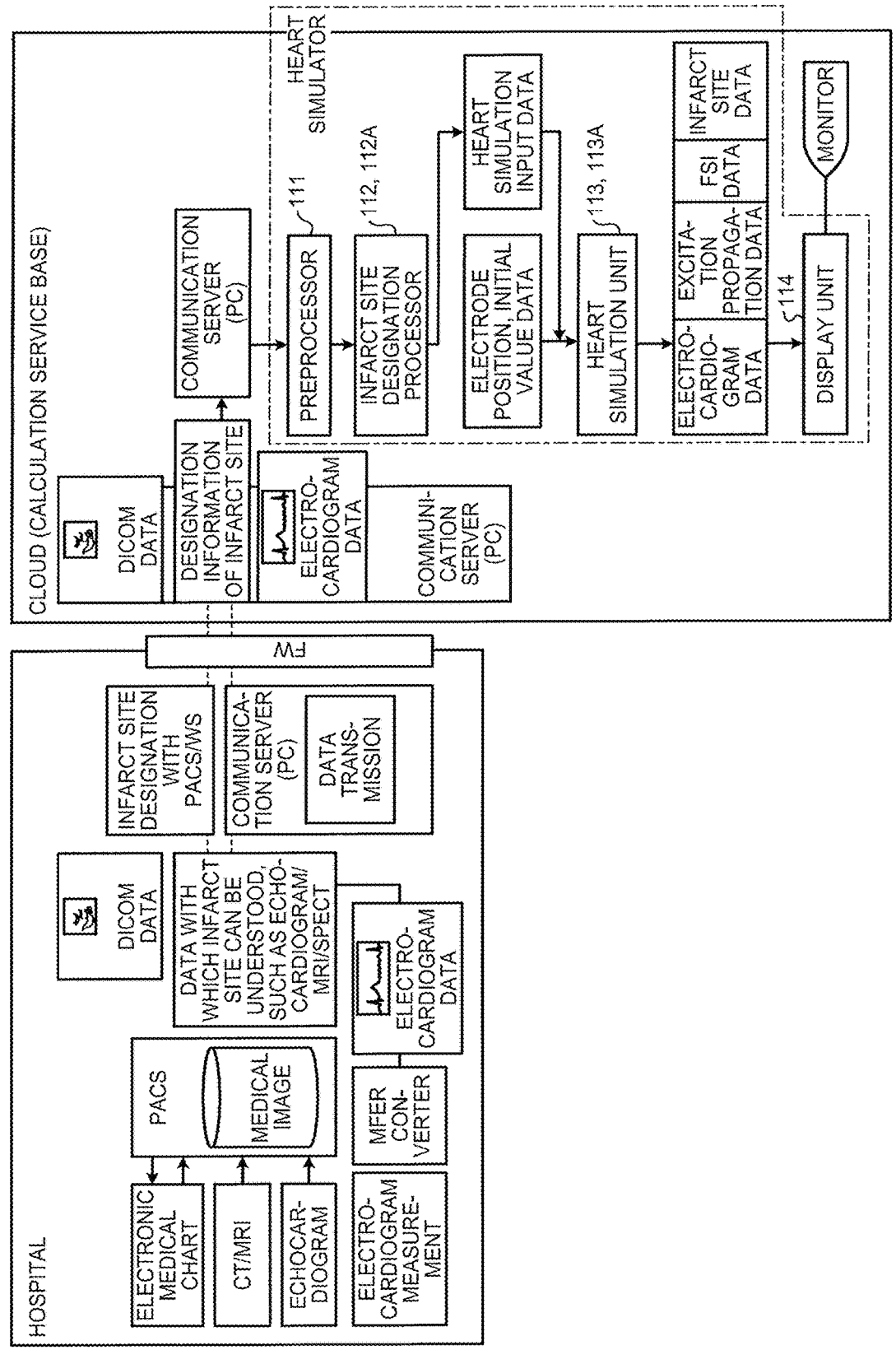
FIG. 18 is a diagram illustrating an application of the infarct site designation processing.

The infarct site designation processing is performed at a calculation service base of the cloud in this case. FIG. 18 is a diagram illustrating an example of an application of the infarct site designation processing. As illustrated in FIG. 18, a hospital is connected to the cloud. The cloud calculation service base receives designation information on an infarct site from the hospital and transfers the received designation information on the infarct site to a heart simulator through a communication server. It is sufficient that the heart simulator uses the designation information on the infarct site to perform the processing of the preprocessor 111 and perform the processing of the infarct site designation processor 112. That is to say, the preprocessor 111 acquires designations of at least two cross-sectional positions. The preprocessor 111 acquires designations of four points (measurement points) indicating two boundaries between an atrium and ventricular myocardium. The preprocessor 111 acquires designations of two points (measurement points) indicating a cardiac axis position and radius information about the cardiac axis position. The infarct site designation processor 112 acquires designations of the specific number of pieces of point information for each of the designated cross sections.

It is sufficient that the heart simulator performs the processing of the heart simulation unit 113 and performs the processing of the display unit 114.

The infarct site designation processing thereby enables a user to efficiently designate the infarct site of the cardiac muscle even on the cloud.

Others

The respective components of the designation device 100 illustrated in the drawings need not be necessarily configured physically as illustrated. That is to say, specific forms of distribution and integration of the designation device 100 are not limited to those illustrated in the drawings, and all or a part of them can be configured to be distributed or integrated functionally or physically based on a desired unit depending on various loads and usage conditions. For example, the preprocessor 111 and the infarct site designation processor 112 may be integrated as one unit. The preprocessor 111 may be separated into a functional unit acquiring the designations of the cross-sectional positions of the ventricle of the heart and a functional unit acquiring the designations of the measurement points. The storage unit 120 may be connected as an external device of the designation device 100 via a network.

Figure 19:
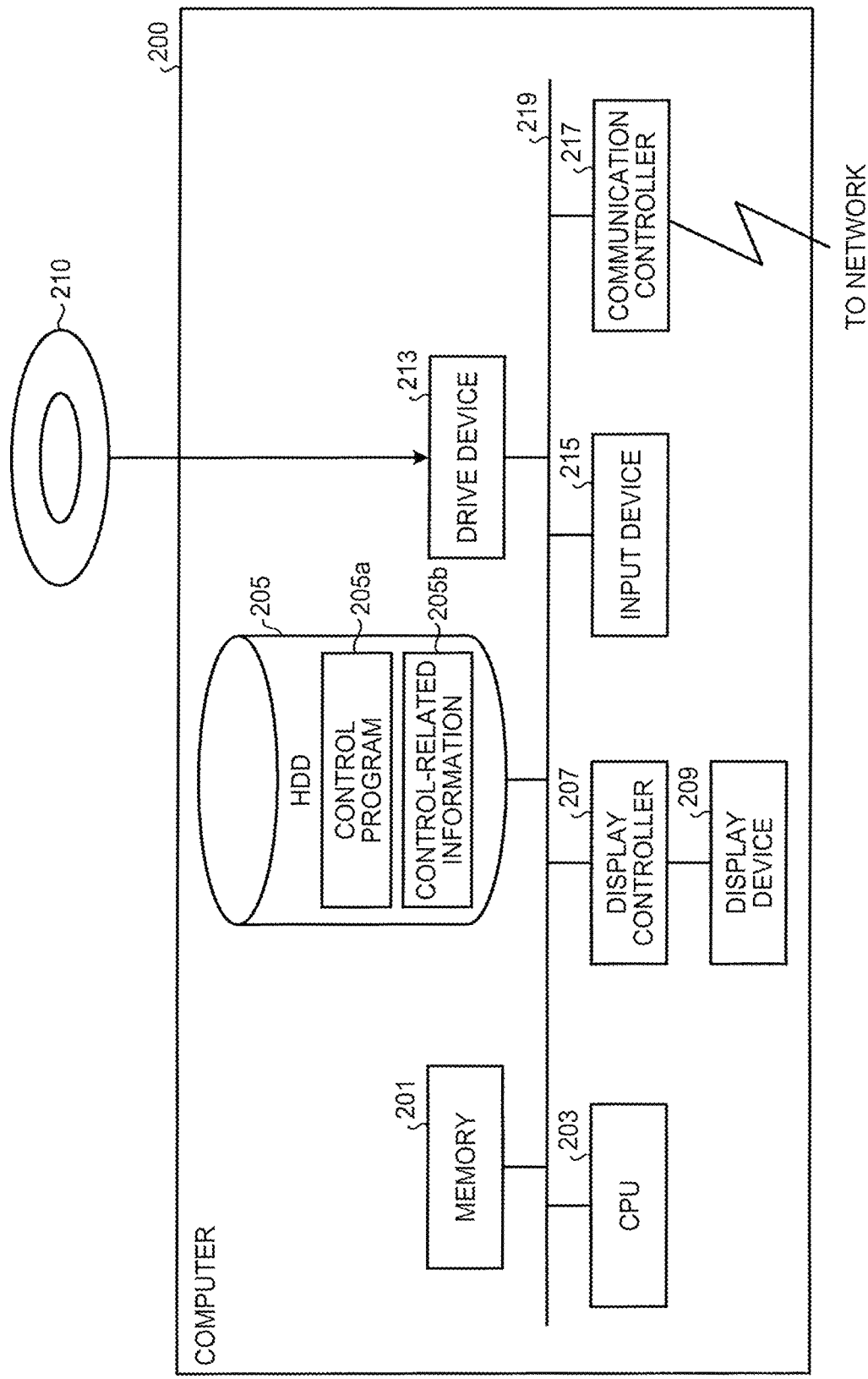
FIG. 19 is a diagram illustrating an example of a computer that executes a designation device control program.

Various pieces of processing described in the abovementioned embodiments can also be implemented by executing a previously prepared program by a computer such as a personal computer and a workstation. Hereinafter, an example of a computer that executes a control program of the designation device 100 will be described, the control program causing the computer to implement similar functions to those of the designation device 100 illustrated in FIG. 1. FIG. 19 is a diagram illustrating an example of the computer that executes the control program of the designation device.

As illustrated in FIG. 19, a computer 200 includes a CPU 203 executing various pieces of operation processing, an input device 215 receiving an input of data from a user, and a display controller 207 controlling a display device 209. The computer 200 includes a drive device 213 reading a program and the like from a storage medium and a communication controller 217 transferring data to and from another computer via a network. The computer 200 includes a memory 201 that temporarily stored therein various pieces of information and a hard disk drive (HDD) 205. The memory 201, the CPU 203, the HDD 205, the display controller 207, the drive device 213, the input device 215, and the communication controller 217 are connected to one another via a bus 219.

The drive device 213 is, for example, a device for a removable disk 210. The HDD 205 stores therein a control program 205a and control-related information 205b.

The CPU 203 reads and loads the control program 205a on the memory 201 and executes it as a process. The process corresponds to various functional units of the designation device 100. The control-related information 205b corresponds to the nonstructural lattice data storage unit 121 and the infarct site element list 122. For example, the removable disk 210 stores therein various pieces of information such as the control program 205a.

The control program 205a is not necessarily stored in the HDD 205 from the first. The program is stored in, for example, a "portable physical medium", such as a flexible disk (FD), a compact disc read only memory (CD-ROM), a digital versatile disc (DVD), a magneto-optical disc, and an integrated circuit (IC) card, that is inserted into the computer 200. The computer 200 may read and execute the control program 205a therefrom.

According to an embodiment, an infarct site of cardiac muscle can be efficiently designated.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A designation device comprising:
    a storage that stores therein a three-dimensional model of an organ; and
    a processor coupled to the storage, wherein the processor executes a process comprising:
    first acquiring, from a user, designation of positions of cross sections of the three-dimensional model of the organ;
    second acquiring, from a user, designation of a specific number of pieces of point information, the pieces of point information indicating positions of an infarct site of the organ on at least two cross sections among the cross sections;
    determining positions of the infarct site of the organ that is interposed between the at least two cross sections on the basis of the three-dimensional model of the organ and the pieces of point information; and outputting an image reproducing determination result of the determined positions of the infarct site of the organ using the three-dimensional model, wherein:

the first acquiring includes designation of a first mapping plane of an inner membrane and a second mapping plane of an outer membrane of the three-dimensional model of the organ;

the second acquiring includes designation of another specific number of pieces of point information, the pieces of point information indicating positions of the infarct site of the organ on each of the first mapping plane and the second mapping plane; and the determining includes determining positions of the infarct site of the organ that is interposed between the first mapping plane and the second mapping plane on the basis of the pieces of point information designated on each of the first mapping plane and the second mapping plane.

2. The designation device according to claim 1, wherein the second acquiring includes acquiring, for one of on a first cross section among the cross sections, designation of the specific number of pieces of point information among pieces of point information defined on the cross section previously or by designation.

3. The designation device according to claim 2, wherein the determining includes determining the positions of the infarct site of the organ that is interposed between the first cross section and a second cross section on the basis of the pieces of point information designated for the first cross section and pieces of point information designated for the a second cross section corresponding to the pieces of point information.

4. A designation device comprising:
a storage that stores therein a three-dimensional model of an organ; and
a processor coupled to the storage, wherein the processor executes a process including:
  first acquiring designation of a first mapping plane of an inner membrane and a second mapping plane of an outer membrane of the three-dimensional model of the organ;
  second acquiring designation of a specific number of pieces of point information, the pieces of point information indicating positions of an infarct site of the organ on each of the first mapping plane and the second mapping plane;
  determining positions of the infarct site of the organ that is interposed between the first mapping plane and the second mapping plane on the basis of the pieces of point information designated on each of the first mapping plane and the second mapping plane; and
  outputting an image reproducing the determined positions of the infarct site of the organ using the three-dimensional model.

5. The designation device according to claim 4, wherein the second acquiring includes acquiring designation of the specific number of pieces of point information, the pieces of point information indicating a range that is estimated to be the infarct site of the organ on each of the first mapping plane and the second mapping plane.

6. The designation device according to claim 1, wherein the organ is a heart.

7. A non-transitory computer-readable recording medium having stored therein a designation device control program that causes a computer to execute a process, the process comprising:

storing a three-dimensional model of an organ;

first acquiring, from a user, designation of positions of cross sections of the three-dimensional model of the organ;

second acquiring, from the user, designation of a specific number of pieces of point information, the pieces of point information indicating positions of an infarct site of the organ on at least two cross sections among the cross sections;

determining positions of the infarct site of the organ that is interposed between the at least two cross sections on the basis of the three-dimensional model of the organ and the pieces of point information; and outputting an image reproducing the determined positions of the infarct site of the organ using the three-dimensional model, wherein:

the first acquiring includes designation of a first mapping plane of an inner membrane and a second mapping plane of an outer membrane of the three-dimensional model of the organ;

the second acquiring includes designation of another specific number of pieces of point information, the pieces of point information indicating positions of the infarct site of the organ on each of the first mapping plane and the second mapping plane; and the determining includes determining positions of the infarct site of the organ that is interposed between the first mapping plane and the second mapping plane on the basis of the pieces of point information designated on each of the first mapping plane and the second mapping plane.

8. A designation device control method comprising:

storing, by a processor, a three-dimensional model of an organ;

first acquiring, by the processor, from a user, designation of positions of cross sections of the three-dimensional model of the organ;

second acquiring, by the processor, from the user, designation of a specific number of pieces of point information, the pieces of point information indicating positions of an infarct site of the organ on at least two cross sections among the cross sections;

determining, by the processor, positions of the infarct site of the organ that is interposed between the at least two cross sections on the basis of the three-dimensional model of the organ and the pieces of point information; and outputting, by the processor, an image reproducing the determined positions of the infarct site of the organ using the three-dimensional model, wherein:

the first acquiring includes designation of a first mapping plane of an inner membrane and a second mapping plane of an outer membrane of the three-dimensional model of the organ;

the second acquiring includes designation of another specific number of pieces of point information, the pieces of point information indicating positions of the infarct site of the organ on each of the first mapping plane and the second mapping plane; and the determining includes determining positions of the infarct site of the organ that is interposed between the first mapping plane and the second mapping plane on the basis of the pieces of point information designated on each of the first mapping plane and the second mapping plane.

9. The designation device according to claim 4, wherein the organ is a heart.

10. A non-transitory computer-readable recording medium having stored therein a designation device control program that causes a computer to execute a process, the process comprising:
- storing a three-dimensional model of an organ;
- first acquiring designation of a first mapping plane of an inner membrane and a second mapping plane of an outer membrane of the three-dimensional model of the organ;
- second acquiring designation of a specific number of pieces of point information, the pieces of point information indicating a range that is estimated to be an infarct site of the organ on each of the first mapping plane and the second mapping plane, the pieces of point information indicating an infarct site of the organ on each of the first mapping plane and the second mapping plane;
- determining positions of the infarct site of the organ that is interposed between the first mapping plane and the second mapping plane on the basis of the pieces of point information designated on each of the first mapping plane and the second mapping plane; and
- outputting an image reproducing the determined positions of the infarct site of the organ using the three-dimensional model, wherein:
- the first acquiring includes designation of a first mapping plane of an inner membrane and a second mapping plane of an outer membrane of the three-dimensional model of the organ;
- the second acquiring includes designation of another specific number of pieces of point information, the pieces of point information indicating positions of the infarct site of the organ on each of the first mapping plane and the second mapping plane; and
- the determining includes determining positions of the infarct site of the organ that is interposed between the first mapping plane and the second mapping plane on the basis of the pieces of point information designated on each of the first mapping plane and the second mapping plane.

11. A designation device control method comprising:
- storing, by a processor, a three-dimensional model of an organ;
- first acquiring, by the processor, designation of a first mapping plane of an inner membrane and a second mapping plane of an outer membrane of the three-dimensional model of the organ;
- second acquiring, by the processor, designation of a specific number of pieces of point information, the pieces of point information indicating a range that is estimated to be an infarct site of the organ on each of the first mapping plane and the second mapping, the pieces of point information indicating an infarct site of the organ on each of the first mapping plane and the second mapping plane;
- determining, by the processor, positions of the infarct site of the organ that is interposed between the first mapping plane and the second mapping plane on the basis of the pieces of point information designated on each of the first mapping plane and the second mapping plane; and
- outputting, by the processor an image reproducing the determined positions of the infarct site of the organ using the three-dimensional model, wherein:
- the first acquiring includes designation of a first mapping plane of an inner membrane and a second mapping plane of an outer membrane of the three-dimensional model of the organ;
- the second acquiring includes designation of another specific number of pieces of point information, the pieces of point information indicating positions of the infarct site of the organ on each of the first mapping plane and the second mapping plane; and
- the determining includes determining positions of the infarct site of the organ that is interposed between the first mapping plane and the second mapping plane on the basis of the pieces of point information designated on each of the first mapping plane and the second mapping plane.

* * * * *